US009883824B2

(12) United States Patent
Tiao et al.

(10) Patent No.: US 9,883,824 B2
(45) Date of Patent: Feb. 6, 2018

(54) DETECTING DEVICE

(71) Applicant: Taiwan Biophotonic Corporation, Hsinchu (TW)

(72) Inventors: Kuo-Tung Tiao, Hsinchu County (TW); Jyh-Chern Chen, New Taipei (TW); Yu-Tang Li, New Taipei (TW); Chang-Sheng Chu, Hsinchu (TW); Shuang-Chao Chung, Hsinchu County (TW); Chih-Hsun Fan, Hsinchu (TW); Ming-Chia Li, Taichung (TW)

(73) Assignee: Taiwan Biophotonic Corporation, Hsinchu (TW)

( * ) Notice: Subject to any disclaimer, the term of this patent is extended or adjusted under 35 U.S.C. 154(b) by 601 days.

(21) Appl. No.: 13/970,613

(22) Filed: Aug. 20, 2013

(65) Prior Publication Data

US 2014/0051955 A1 Feb. 20, 2014

Related U.S. Application Data

(60) Provisional application No. 61/684,819, filed on Aug. 20, 2012.

(30) Foreign Application Priority Data

Jul. 30, 2013 (TW) ................................. 102127307

(51) Int. Cl.
*A61B 5/1455* (2006.01)
*A61B 5/00* (2006.01)

(52) U.S. Cl.
CPC ........ *A61B 5/14552* (2013.01); *A61B 5/1455* (2013.01); *A61B 5/00* (2013.01)

(58) Field of Classification Search
None
See application file for complete search history.

(56) References Cited

U.S. PATENT DOCUMENTS 4,867,557 A 9/1989 Takatani et al.
4,877,322 A 10/1989 Hill
(Continued)

FOREIGN PATENT DOCUMENTS

CA 1258384 A1 8/1989
CA 2537370 A1 3/2005
(Continued)

OTHER PUBLICATIONS

Matthew Pinto, "Oximeter"(https://wiki.engr.illinois.edu/display/BIOE414/Oximeter), Dec. 16, 2010, pp. 1-2.
(Continued)

*Primary Examiner* — Eric Winakur
*Assistant Examiner* — Marjan Fardanesh
(74) *Attorney, Agent, or Firm* — Chieh-Mei Wang

(57) ABSTRACT

A detecting device includes at least one detecting module. In the detecting module, a light source unit is configured to emit a first beam and a second beam. The wavelength of the first beam is different from that of the second beam. A packaging unit is disposed on the light source unit and a light detecting unit and on transmission paths of the first beam and the second beam from the light source unit. An optical microstructure unit is disposed on the transmission paths of the first beam and the second beam. The first beam and the second beam emitted from the light source unit pass through the packaging unit to pass the optical microstructure unit to be transmitted to a biological tissue, and then pass through the optical microstructure unit to pass the packaging unit to be transmitted to the light detecting unit in sequence.

17 Claims, 9 Drawing Sheets

(56) References Cited

U.S. PATENT DOCUMENTS

| | | | |
|---|---|---|---|
| 4,880,304 A | 11/1989 | Jaeb et al. | |
| 5,357,954 A | 10/1994 | Shigezawa et al. | |
| 5,584,296 A | 12/1996 | Cui et al. | |
| 5,647,359 A | 7/1997 | Kohno et al. | |
| 6,177,984 B1 * | 1/2001 | Jacques | G01J 4/00 356/338 |
| 6,181,959 B1 | 1/2001 | Schollermann et al. | |
| 6,763,256 B2 | 7/2004 | Kimball et al. | |
| 6,839,585 B2 | 1/2005 | Lowery et al. | |
| 6,859,658 B1 | 2/2005 | Krug | |
| 6,879,850 B2 | 4/2005 | Kimball | |
| 7,356,365 B2 | 4/2008 | Schurman | |
| 7,822,453 B2 | 10/2010 | Mannheimer et al. | |
| 8,116,851 B2 | 2/2012 | Cho et al. | |
| 8,175,667 B2 | 5/2012 | Debreczeny | |
| 8,311,601 B2 | 11/2012 | Besko | |
| 8,386,000 B2 | 2/2013 | McKenna | |
| 2003/0139672 A1 | 7/2003 | Cane et al. | |
| 2004/0082842 A1 | 4/2004 | Lumba et al. | |
| 2004/0225206 A1 | 11/2004 | Kouchnir | |
| 2005/0267346 A1 | 12/2005 | Faber et al. | |
| 2006/0193550 A1 | 8/2006 | Wawro et al. | |
| 2007/0038126 A1 | 2/2007 | Pyle et al. | |
| 2007/0060809 A1 | 3/2007 | Higgins | |
| 2008/0017800 A1 | 1/2008 | Benni | |
| 2009/0182209 A1 | 7/2009 | Benni | |
| 2010/0004719 A1 | 1/2010 | Hamada et al. | |
| 2010/0022856 A1 | 1/2010 | Cinbis et al. | |
| 2012/0044484 A1 | 2/2012 | Henneberg | |
| 2012/0253153 A1 | 10/2012 | Trumble | |
| 2013/0043551 A1 | 2/2013 | Yoshizawa | |

FOREIGN PATENT DOCUMENTS

| | | |
|---|---|---|
| CN | 2938079 Y | 8/2007 |
| CN | 101232843 A | 7/2008 |
| CN | 102688024 A | 9/2012 |
| EP | 630203 A1 | 12/1994 |
| EP | 630203 B1 | 7/2002 |
| EP | 2346389 A1 | 7/2011 |
| GB | 1325039 A | 8/1973 |
| JP | 2001509893 A | 7/2001 |
| JP | 3740571 | 2/2006 |
| JP | 2006230657 A | 9/2006 |
| JP | 2009106376 A | 5/2009 |
| JP | 4406560 | 1/2010 |
| JP | 2010155159 A | 7/2010 |
| JP | 4680422 | 5/2011 |
| JP | 2011239863 A | 12/2011 |
| JP | 5028256 | 9/2012 |
| KR | 2012067761 | 6/2012 |
| TW | 200722053 | 6/2007 |
| TW | 201032777 A1 | 9/2010 |
| WO | 1992021280 A1 | 12/1992 |
| WO | 2005010568 A2 | 2/2005 |
| WO | 2010050170 A1 | 5/2010 |
| WO | 2012109661 A2 | 8/2012 |

OTHER PUBLICATIONS

Chin-Chang Hu, "A Preliminary Study of Evaluation System for Muscle Fatigue Based on Oxygen Saturation," Master's Thesis, Jun. 22, 2007, Electrical Engineering Department of National Cheng-Kung University.

Wu Min, et al., "Development of the skin flap blood oximeter", Chinese Medical Equipment Journal, Jan. 2013, pp. 11-13, vol. 24(1), CN.

Yi-Hsuan Wang et al., "A New Oxygen Saturation Images of Iris Tissue," IEEE Conference on Sensors, Nov. 1-4, 2010, pp. 1386-1389.

Hidenobu Arimoto, "Measurement of 2-D SpO2 Distribution in Skin Tissue by Multispectral Imaging with Depth Selectivity Control," Proceedings of the 28th IEEE EMBS Annual International Conference, Aug. 30-Sep. 3, 2006, pp. 1968-1971.

Guowei Di et al., "A Reflectance Pulse Oximeter Design Using the MSP430F149," IEEE/ICME International Conference on Complex Medical Engineering, May 23-27, 2007, pp. 1081-1084.

Damianou, D. and Crowe, J.A., "The Wavelength Dependence of Pulse Oximetry," IEE Colloquium on Pulse Oximetry: A Critical Appraisal, May 29, 1996, pp. 7/1-7/3.

Setsuo Takatani et al., "A Miniature Hybrid Reflection Type Optical Sensor for Measurement of Hemoglobin Content and Oxygen Saturation of Whole Blood," IEEE Transactions on Biomedical Engineering, vol. 35, No. 3, Mar. 1988, pp. 187-198.

Omar Abdallah et al., "Optical Non-invasive Calculation of Hemoglobin Components Concentrations and Fractional oxygen Saturation Using a Ring-Scattering Pulse Oximeter," SPIE Proceedings: Optical Diagnostics and Sensing, vol. 5325, Jun. 18, 2004, pp. 51-61.

R. Holmes et al., "Optical Fibre Based Pulse Oximeter for Monitoring in Magnetic Resonance Scanners," SPIE Proceedings: Tenth International Conference on Optical Fibre Sensors, vol. 2360, Sep. 14, 1994, pp. 94-97.

Sergio Fantini et al., "Frequency-Domain Multisource Optical Spectrometer and Oximeter," SPIE Proceedings: Photon Transport in Highly Scattering Tissue, vol. 2326, Jan. 31, 1995, pp. 108-116.

Maria Angela Franceschini et al., "Optical Study of the Skeletal Muscle During Exercise with a Second-Generation Frequency-Domain Tissue Oximeter," SPIE Proceedings: Optical Tomography and Spectroscopy of Tissue: Theory, Instrumentation, Model, and Human Studies II, vol. 2979, Aug. 18, 1997, pp. 807-814.

M. M. Asimov et al., "High Sensitive Pulse Oximeter-Spectrophotometer for Laser-Optical Dosimetry in Biology and Medicine," SPIE Proceedings: Laser for Measurements and Information Transfer, vol. 6251, Apr. 18, 2006, 1997, pp. 1-8.

Justin P. Phillips et al., "Investigation of an optical fiber cerebral oximeter using a Monte Carlo model," Proceedings of the 29th Annual International Conference of the IEEE EMBS, Aug. 23-26, 2007, pp. 1113-1116.

Katsuyuki Sakamoto et al., "Optical Characteristics of Flowing Blood: Effects on the Pulse Oximeter," Proceedings of the 29th Annual International Conference of the IEEE EMBS, Aug. 23-26, 2007, pp. 4552-4555.

K Rais-Bahrami et al., "Validation of a noninvasive neonatal optical cerebral oximeter in veno-venous ECMO patients with a cephalad catheter," Journal of Perinatology, Aug. 10, 2006, pp. 628-635.

Lorenzo Scalise et al., "Rejection of false saturation data in optical pulse-oximeter," SPIE Proceedings: Biophotonics: Photonic Solutions for Better Health Care II, vol. 7715, May 14, 2010, pp. 1-8.

Yu Shang et al., "Portable optical tissue flow oximeter based on diffuse correlation spectroscopy," Optics Letters, vol. 34, No. 22, Nov. 15, 2009, pp. 3556-3558.

E. Dominguez De Villota et al., Abstract of "The Influence of Carboxyhaemoglobin on the Oxygen-Binding Capacity of Blood, A comparison of manometric (Van Slyke) and optical (Co-Oximeter) measurements", British Journal of Anaesthesia, Feb. 1976, pp. 1.

Ni Pq et al., Abstract of "Research on digital pulse oximeter based on optical frequency converter", 10th World Congress on Intelligent Control and Automation (WCICA), Jul. 6-8, 2012, pp. 1-2.

Guoqiang Yu et al., Abstract of "Portable Optical Tissue Flow Oximeter for Evaluation of Revascularization Effect on Ischemic Muscle Hemodynamics", Biomedical Optics and 3-D Imaging, Apr. 12-14, 2010, pp. 1-2.

G. Litscher et al., Abstract of "Transcranial Optical Spectroscopy—A comparison of the TOS 96 and INVOS 3100 cerebral oximeters. Transkranielle optische Spektroskopie—ein Vergleich der zerebralen Oximeter TOS 96 and INVOS 3100", Biomedical Engineering, vol. 43, Issue 5, Jul. 17, 2009, pp. 1-4.

He L. et al., Abstract of "Using optical fibers with different modes to improve the signal-to-noise ratio of diffuse correlation spectroscopy flow-oximeter measurements", J Biomed Opt., Mar. 2013, pp. 1.

* cited by examiner

DETECTING DEVICE

CROSS-REFERENCE TO RELATED APPLICATION

This application claims the priority benefits of U.S. provisional application Ser. No. 61/684,819, filed on Aug. 20, 2012 and Taiwan application serial no. 102127307, filed on Jul. 30, 2013. The entirety of each of the above-mentioned patent applications is hereby incorporated by reference herein and made a part of this specification.

TECHNICAL FIELD

The technical field relates to a detecting device.

BACKGROUND

Apparatuses and devices for measuring physiological parameters of organism or human body by utilizing various optical principles are gradually matured along with the advances in optical-electronic technologies. Generally, a non-invasive measurement can be accomplished by using an optical principle measuring technology, which offers important contributions and application values in medical or biological field, for it can effectively prevent infections or contagious diseases.

A conventional reflective oximeter is utilized to infiltrate an infrared light and a near infrared light into human body, and measure a light signal being returned. Later, a signal processor is utilized to calculate a blood oxygenation saturation by comparing absorption proportions of oxyhemoglobin ($HbO_2$) and deoxyhemoglobin (Hb) for the infrared light and the near infrared light. Two major elements in the oximeter include one being a hardware measuring device for emitting and receiving the light signal and converting the light signal being received into an electrical signal; and another one being a display hardware and a software thereof in which blood oxygen values can be calculated. Since the measuring device often requires to be contacted to surfaces of human body, noises may be generated due to movements of the human body or changes in physiological conditions, which is prone to wrong blood oxygen values. Accordingly, the oximeter usually requires a software to filter out the noises, so as to ensure an accuracy of the value being read.

SUMMARY

One of exemplary embodiments provides a detecting device configured to detect a physiological parameter of a biological tissue. The detecting device comprises at least one detecting module, and the detecting module comprises a light source unit, a light detecting unit, a packaging unit and an optical microstructure unit. The light source unit is configured to emit a first beam and a second beam, in which a wavelength of the first beam is different from a wavelength of the second beam. The packaging unit is disposed on the light source unit and the light detecting unit and located on transmission paths of the first beam and the second beam from the light source unit. The optical microstructure unit is disposed on the transmission paths of the first beam and the second beam. The first beam and the second beam emitted from the light source unit pass through the packaging unit, pass through the optical microstructure unit, are transmitted to a biological tissue, pass through the optical microstructure unit, pass the packaging unit, and are transmitted to the light detecting unit in sequence.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMB0DIMENTS

Figure 1A:
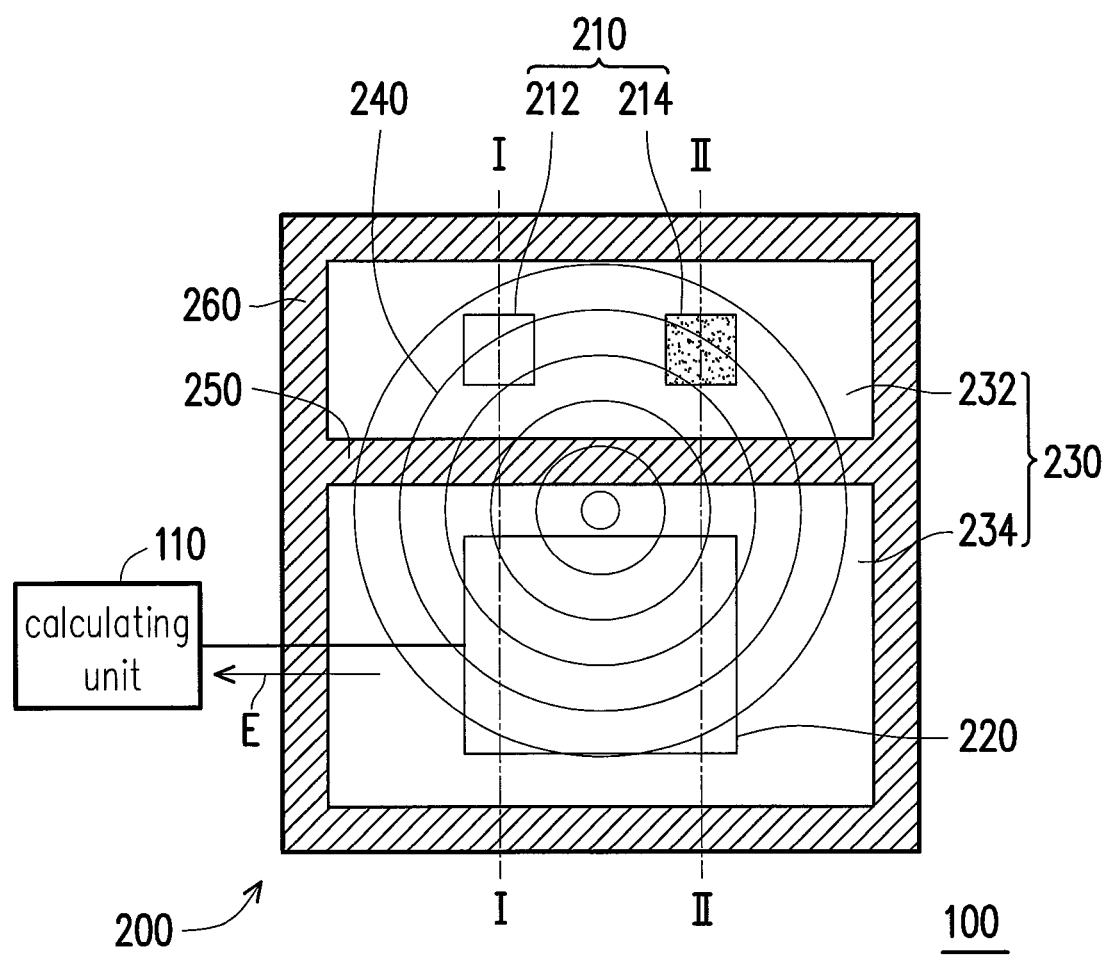
FIG. 1A is a bottom schematic view of a detecting device according to an embodiment of the disclosure.
Figure 1B:
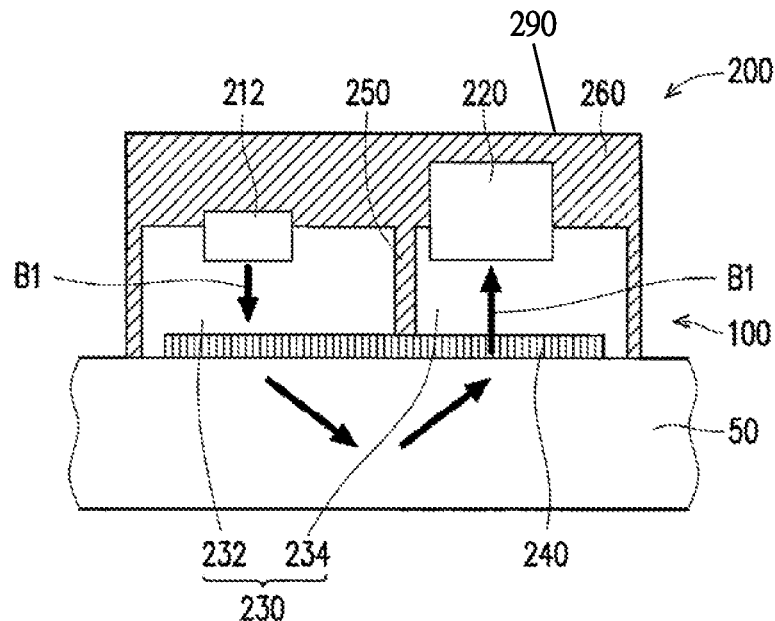
FIG. 1B is a schematic cross-sectional view of the detecting device of FIG. 1A along line I-I.
Figure 1C:
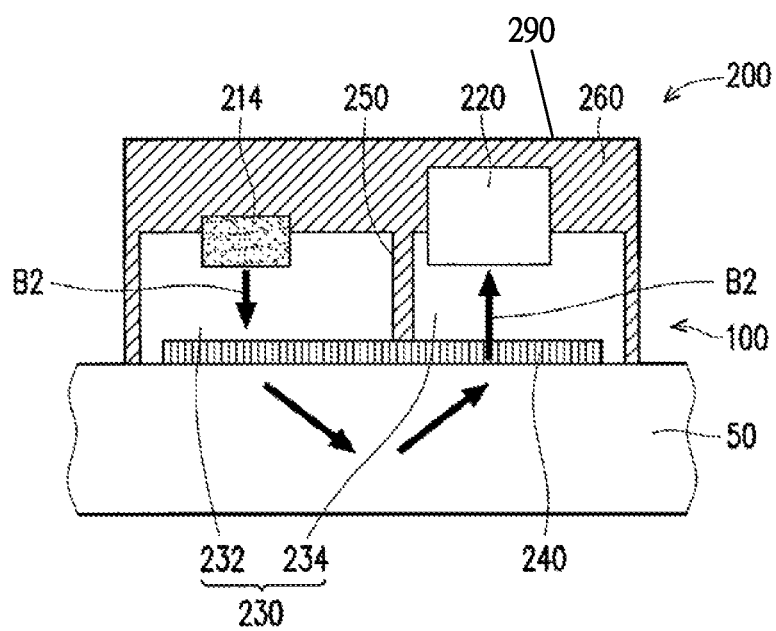
FIG. 1C is a schematic cross-sectional view of the detecting device of FIG. 1A along line II-II.

FIG. 1A is a bottom schematic view of a detecting device according to an embodiment of the disclosure. FIG. 1B is a schematic cross-sectional view of the detecting device of FIG. 1A along line I-I. FIG. 1C is a schematic cross-sectional view of the detecting device of FIG. 1A along line II-II. Referring to FIG. 1A to FIG. 1C, a detecting device 100 of the present embodiment is configured to detect a physiological parameter of a biological tissue 50. For instance, the biological tissue 50 is, for example, human or animal skin, and the physiological parameter is, for example, a blood oxygenation. The detecting device 100 comprises at least one detecting module 200 (one detecting module 200 is illustrated in the present embodiment as an example), and the detecting module 200 comprises a light source unit 210, a light detecting unit 220, a packaging unit 230 and an optical microstructure unit 240. The light source unit 210 is configured to emit a first beam B1 (as illustrated in FIG. 1B) and a second beam B2 (as illustrated in FIG. 1C), and a wavelength of the first beam B1 is different from a wavelength of the second beam B2. In the present embodiment, the wavelengths of the first beam B1 and the second beam B2 fall within wavelength ranges of a red light and an infrared light. For instance, the first beam B1 is the red light with the wavelength being, for example, 660 nm; and the second beam B2 is the infrared light with the wavelength being, for example, 910 nm. Alternatively, in another embodiment, the first beam B1 can be the infrared light and the second beam B2 is the red light. Moreover, in other embodiments, the wavelengths of the first beam B1 and the second beam B2 fall within the wavelength range of other visible light or other invisible light.

In the present embodiment, the light source unit 210 comprises a first light-emitting element 212 and a second light-emitting element 214. The first light-emitting element 212 is configured to emit the beam B1, and the second light-emitting element 214 is configured to emit the second beam B2. In the present embodiment, the first light-emitting element 212 and the second light-emitting element 214 alternately emit the first beam B1 and the second beam B2. In the present embodiment, the light source unit 210 comprises a light-emitting diode, which means that the first light-emitting element 212 and the second light-emitting element 214 are, for example, light-emitting diodes. However, in other embodiments, the first light-emitting element 212 and the second light-emitting element 214 can also be organic light-emitting diodes (OLEDs) or laser diodes. Furthermore, in the present embodiment, the light detecting unit 220 is a light detector being, for example, a photodiode.

The packaging unit 230 is disposed on the light source unit 210 and the light detecting unit 220 and located on transmission paths of the first beam B1 and the second beam B2 from the light source unit 210. In the present embodiment, the packaging unit 230 is capable of being penetrated by the first beam B1 and the second beam B2. For instance, in the present embodiment, the packaging unit 230 is capable of being penetrated by the infrared light and the read light. However, in other embodiments, the packaging unit 230 can also be penetrated by the infrared light and the visible light. Furthermore, in the present embodiment, the packaging unit 230 comprises a waveguide, which covers the light source unit 210 and the light detecting unit 220. More specifically, in the present embodiment, the packaging unit 230 comprises a first waveguide 232 and a second waveguide 234. The first waveguide 232 covers the light source unit 210, and the second waveguide 234 covers the light detecting unit 220.

The optical microstructure unit 240 is disposed on the transmission paths of the first beam B1 and the second beam B2. The first beam B1 and the second beam B2 emitted from the light source unit 210 pass through the packaging unit 230, pass through the optical microstructure unit 240, are transmitted to a biological tissue 50, pass through the optical microstructure unit 240, pass through the packaging unit 230, and are transmitted to the light detecting unit 220 in sequence. In the present embodiment, the optical microstructure unit 240 is a diffractive optical element (DOE) structure. Furthermore, in the present embodiment, the optical microstructure unit 240 is a surface microstructure of the packaging unit 230, and more specifically, the optical microstructure unit 240 directly forms on the surface of the packaging unit 230. However, in another embodiment, the optical microstructure unit 240 can be an optical film, and the optical microstructure unit 240 is mounted on the packaging unit 230 (e.g., attached to or leaned against the packaging unit 230). In other words, the optical microstructure unit 240 can also be a diffractive optical element attached to or leaned against the packaging unit 230. Furthermore, in other embodiments, the optical microstructure unit 240 can also be a holographic optical element (HOE, a computer-generated holographic optical element structure, a fresnel lens structure or a lens) grating.

In the present embodiment, the light source unit 210 and the light detecting unit 220 are located on an identical side of the biological tissue 50. More specifically, the first beam B1 and the second beam B2 from the light source unit 210 is guided by the first waveguide 232 to be transmitted to the optical microstructure unit 240. In this case, the optical microstructure unit 240 diffracts the first beam B1 and the second beam B2. With proper design of the diffractive structure of the optical microstructure unit 240, energies of the first beam B1 and the second beam B2 after being diffracted can be concentrated into a diffractive light in one specific diffractive order (e.g., the diffractive light in −1 order or +1 order). Accordingly, the first beam B1 and the second beam B2 can be concentratedly irradiated on the biological tissue 50. For instance, the first beam B1 and the second beam B2 can be concentratedly irradiated on microvascular in dermis of human skin. Next, the biological tissue 50 scatters and reflects the first beam B1 and the second beam B2 to the optical microstructure unit 240. Subsequently, the optical microstructure unit 240 diffracts the first beam B1 and the second beam B2 to the second waveguide 234, and then the second waveguide 234 guides the first beam B1 and the second beam B2 to the light detecting unit 220. With proper design of the diffractive structure of the optical microstructure unit 240, energies of the first beam B1 and the second beam B2 after being diffracted can be concentrated into a diffractive light in one specific diffractive order (e.g., the diffractive light in −1 order or +1 order). Accordingly, the first beam B1 and the second beam B2 can be concentratedly irradiated on the light detecting unit 220 after being diffracted by the optical microstructure unit 240 and being guided by the second waveguide 234. As a result, in the present embodiment, the first beam B1 and the second beam B2 from the light source unit 210 are concentratedly irradiated on the biological tissue 50, and the first beam B1 and the second beam B2 reflected and scattered from the biological tissue 50 are also concentratedly irradiated on the light detecting unit 220. Therefore, noises of light detected by the light detecting unit 220 can become less, namely, a signal-noise ratio thereof is higher. Accordingly, an electrical signal converted from light detected by the light detecting unit 220 can be more correctly and accurately in respond to light intensities of the first beam B1 and the second beam B2, so as to effectively reduce an error rate of the detecting device 100 thereby improving accuracy and reliability of the detecting device 100. In the present embodiment, a pitch between the optical microstructures in the optical microstructure unit 240 (e.g., a pitch between two adjacent ring shape strips in the optical microstructure unit 240 depicted in FIG. 1A, namely, a pitch between two adjacent strips in the diffractive optical element) falls, for example, within a range from 0.05 to 100 μm.

Figure 2:
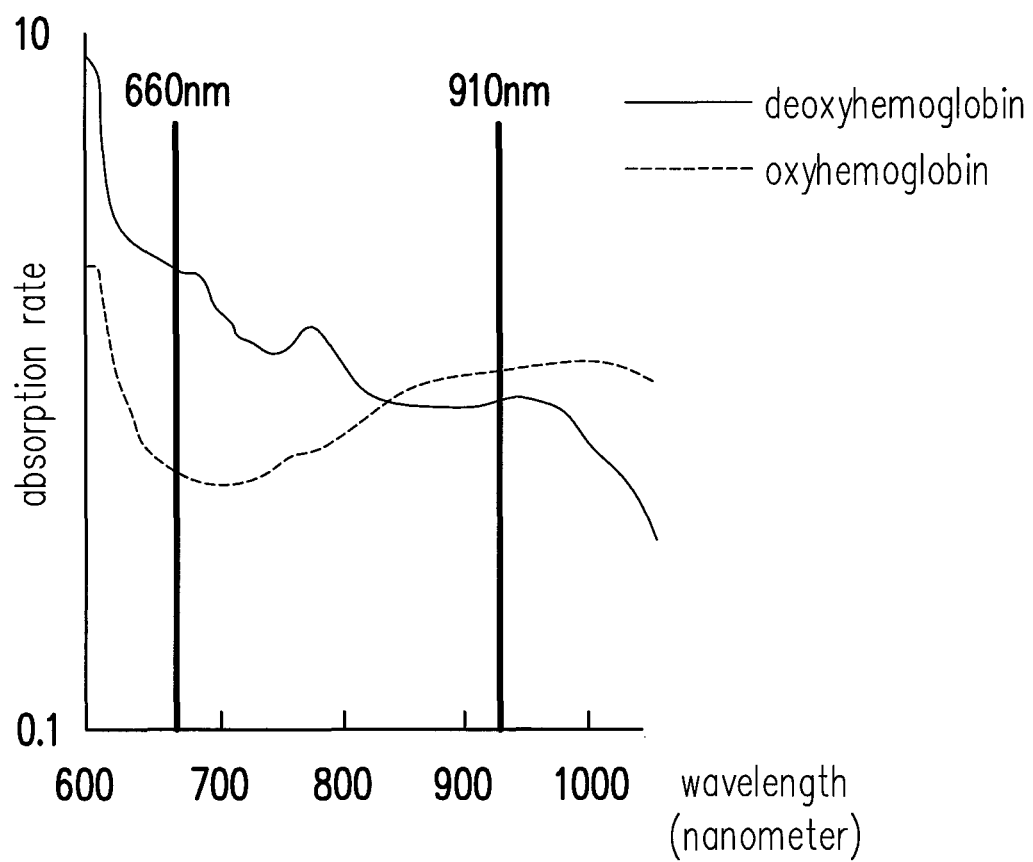
FIG. 2 is an absorption spectrum diagram of oxyhemoglobin and deoxyhemoglobin in human body.

FIG. 2 is an absorption spectrum diagram of oxyhemoglobin and deoxyhemoglobin in human body. Referring to FIG. 1A to FIG. 1C and FIG. 2, the detecting device 100 of the present embodiment can be used to detect a blood oxygenation of microvascular in dermis of human skin. In view of FIG. 2, it can be known that the absorption spectrums of oxyhemoglobin and deoxyhemoglobin are different, thus absorption rates of oxyhemoglobin and deoxyhemoglobin for the red light with the wavelength of 660 nm (i.e. the first beam B1) and the infrared light with the wavelength of 910 nm (i.e. the second beam B2) are different. For the red light with the wavelength of 660 nm, the absorption rate for deoxyhemoglobin is higher than the absorption rate for oxyhemoglobin. However, for the infrared light with the wavelength of 910 nm, the absorption rate for oxyhemoglobin is higher than the absorption rate for deoxyhemoglobin. Therefore, when a concentration ratio between oxyhemoglobin and deoxyhemoglobin in microvascular gets higher, a light intensity ratio between the first beam B1 and the second beam B2 is higher. On the contrary, when the concentration ratio between oxyhemoglobin and deoxyhemoglobin in microvascular gets lower, the light intensity ratio between the first beam B1 and the second beam B2 is lower. Accordingly, the blood oxygenation in the biological tissue 50 can be obtained by calculating the light intensities of the first beam B1 and the second beam B2 measured by the light detecting unit 220.

In the present embodiment, the detecting device 100 further comprises a calculating unit 110 electrically connected to the light detecting unit 220. The light detecting unit 220 converts the first beam B1 and the second beam B2 being detected into an electrical signal E, and the calculating unit 110 calculates the physiological parameter (the blood oxygenation as in the present embodiment) according to the electrical signal E. Moreover, in the present embodiment, since the first beam B1 and the second beam B2 are alternately emitted, the light intensity detected by the light detecting unit 220 when the first beam B1 being emitted is the light intensity of the first beam B1, and the light intensity detected by the light detecting unit 220 when the second beam B2 being emitted is the light intensity of the second beam B2. According to above-said method, the calculating unit 110 can then determine when is the electrical signal E representing the light intensity of the first beam B1, and when is the electrical signal E representing the light intensity of the second beam B2. In other words, the calculating unit 110 obtains the light intensity of the first beam B1 and the light intensity of the second beam B2 in a manner of time multiplexing.

In the present embodiment, since the signal-noise ratio of the first beam B1 and the second beam B2 measured by the light detecting unit 220 being higher, the detecting device 100 can serve as the oximeter with higher accuracy and reliability. Moreover, as the signal-noise ratio being higher, it is not required for the calculating unit 110 to adopt complex algorithms to reduce the noise, such that manufacturing cost and calculation time of the calculating unit 110 can also be lowered.

In the present embodiment, the detecting module 200 further comprises an outer cover 260 covering the light source unit 210, the light detecting unit 220 and the packaging unit 230. The outer cover 260 is capable of blocking an ambient light from the outside, so as to prevent the light detecting unit 220 from generating noises due to influence of the ambient light. Accordingly, the signal-noise ratio detected by the light detecting unit 220 can be further improved.

Furthermore, in the present embodiment, the detecting module 200 further comprises a light separating unit 250 which separates the first waveguide 232 and the second waveguide 234. The light separating unit 250 can effectively prevent the first beam B1 and the second beam B2 from the light source unit 210 from being transmitted to the light detecting unit 220 without being irradiated on the biological tissue 50, so as to further improve the signal-noise ratio.

Figure 3A:
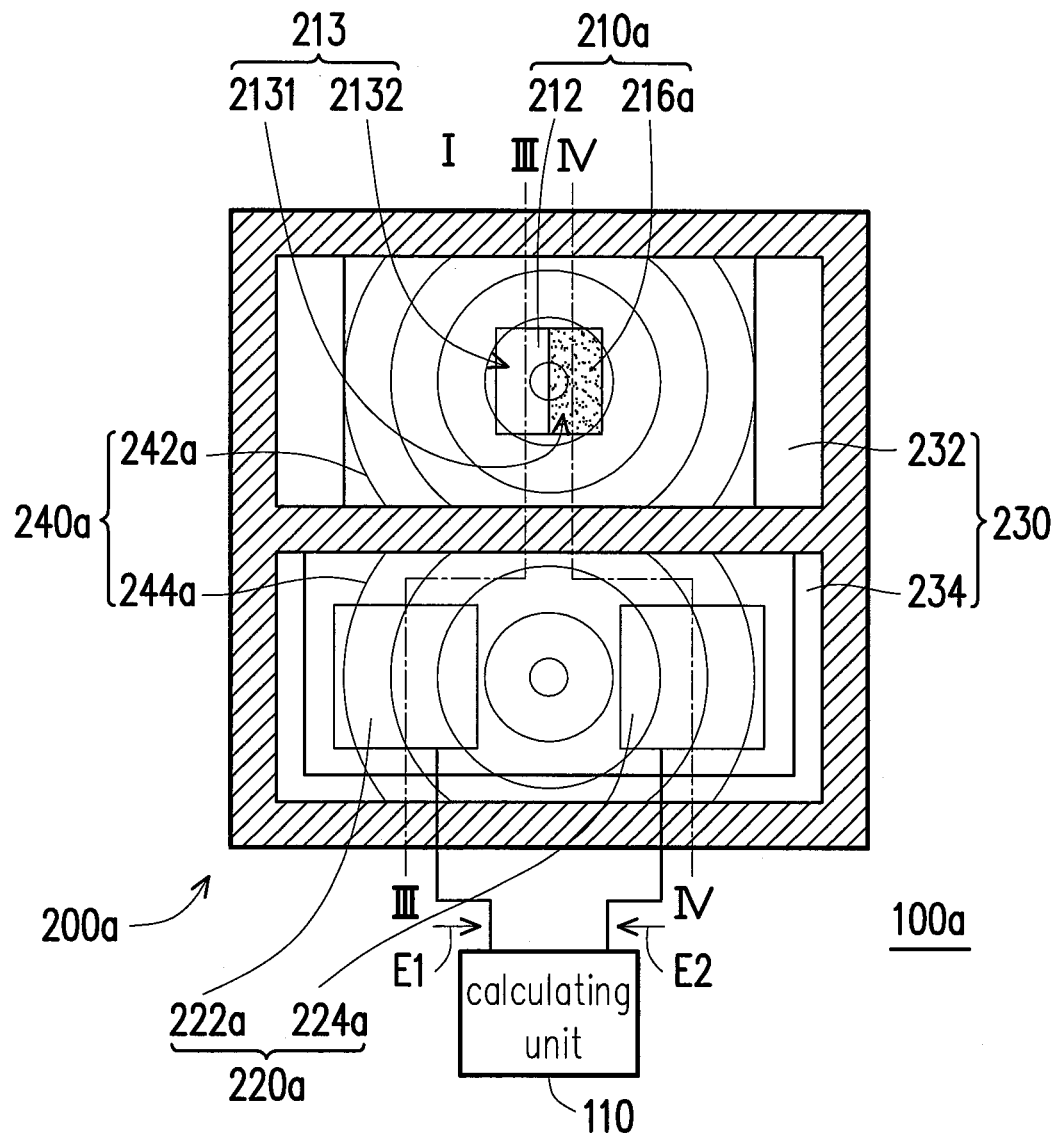
FIG. 3A is a bottom schematic view of a detecting device according to another embodiment of the disclosure.
Figure 3B:
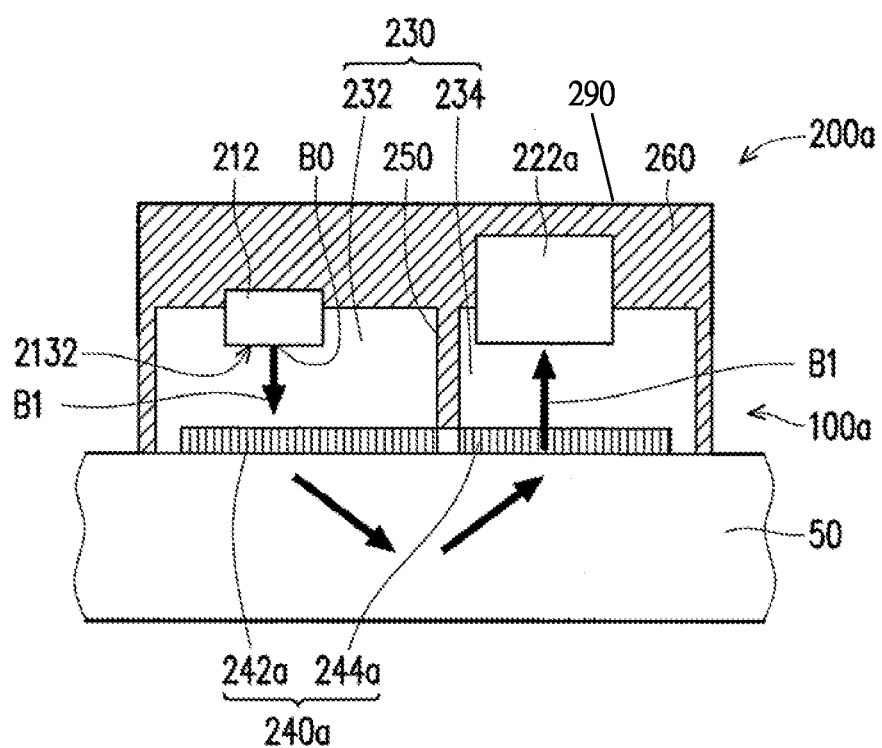
FIG. 3B is a schematic cross-sectional view of the detecting device of FIG. 3A along line
Figure 3C:
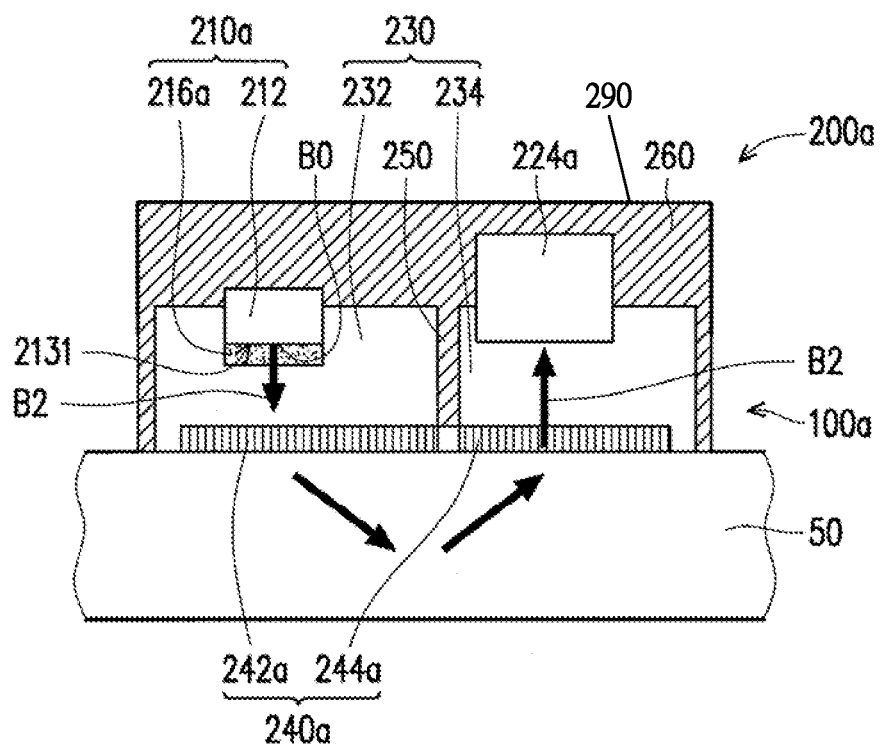
FIG. 3C is a schematic cross-sectional view of the detecting device of FIG. 3A along line IV-IV.

FIG. 3A is a bottom schematic view of a detecting device according to another embodiment of the disclosure. FIG. 3B is a schematic cross-sectional view of the detecting device of FIG. 3A along line III-III. FIG. 3C is a schematic cross-sectional view of the detecting device of FIG. 3A along line IV-IV. Referring to FIG. 3 to FIG. 3C, a detecting device 100a of the present embodiment is similar to the detecting device 100 depicted in FIG. 1A, in which identical reference numerals indicate identical or similar components, and the difference between the two is described as below.

In a detecting module 200a of the detecting device 100a of the present embodiment, a light source unit 210a comprises a first light-emitting element 212 and a wavelength converting material 216a. The first light-emitting element 212 has a light-emitting surface 213 and configured to emit an original beam B0 from the light-emitting surface 213. The wavelength converting material 216a covers a first portion 2131 of the light-emitting surface 213, and exposes a second portion 2132 of the light-emitting surface 213. Therein, at least a part of the original beam B0 emitted by the first portion 2131 is converted into the second beam B2 by the wavelength converting material 216a, and the first beam B1 is formed by the original beam B0 emitted by the second portion 2132. In the present embodiment, a wavelength of the original beam B0 is identical to the wavelength of the first beam B1. In other words, since the original beam B0 emitted by the second portion 2132 does not pass through the wavelength converting material 216a, the original beam B0 of said portion is the first beam B1. In the present embodiment, the wavelength converting material 216a is, for example, a phosphor. However, in other embodiments, the first portion 2131 and the second portion 2132 can also be covered with two different wavelength converting materials, so as to covert the original beam B0 into the first beam B1 and the second beam B2, respectively. In this case, the wavelength of the original beam B0 is smaller than the wavelength of the first beam B1, and is smaller than the wavelength of the second beam B2.

Furthermore, in the present embodiment, a light detecting unit 220a comprises a first light detector 222a and a second light detector 224a. An optical microstructure unit 240a transmits the first beam B1 from the biological tissue 50 to the first light detector 222a, and the optical microstructure unit 240a transmits the second beam B2 from the biological tissue 50 to the second light detector 224a. In the present embodiment, the optical microstructure unit 240a comprises a first optical microstructure 242a and a second optical microstructure 244a. The first optical microstructure 242a is disposed on the transmission paths of the first beam B1 and the second beam B2 from the light source unit 210a, and is configured to transmit the first beam B1 and the second beam B2 from the light source unit 210a to the biological tissue 50. The second optical microstructure 244a is disposed on the transmission paths of the first beam B1 and the second beam B2 from the biological tissue 50, and is configured to transmit the first beam B1 and the second beam B2 from the biological tissue 50 to the light detecting unit 220a.

More specifically, the first optical microstructure 242a concentrates the first beam B1 and the second beam B2 from the first waveguide 232 towards different directions, so as to be irradiated on the biological tissue 50. Furthermore, the first beam B1 and the second beam B2 from the biological tissue 50 are concentrated by the second optical microstructure 244a towards the first light detector 222a and the second light detector 224a, respectively. In other words, the first beam B1 and the second beam B2 can be detected by the first light detector 222a and the second light detector 224a, respectively, thus the light source unit 210a can simultaneously emit the first beam B1 and the second beam B2. In other words, the light detecting unit 220a detects the first beam B1 and the second beam B2 in a manner of spatial multiplexing.

In the present embodiment, the first light detector 222a and the second light detector 224a are, for example, photodiodes, and the first optical microstructure 242a and the second optical microstructure 244a are, for example, a diffractive optical element (DOE) structures. Furthermore, in the present embodiment, the first optical microstructure 242a and the second optical microstructure 244a are, for example, surface microstructures of the first waveguide 232 and the second waveguide 234, respectively. However, in another embodiment, the first optical microstructure 242a and the second optical microstructure 244a can be two optical films, which are mounted on the first waveguide 232 and the second waveguide 234, respectively (e.g., attached to or leaned against the first waveguide 232 and the second waveguide 234, respectively). In other words, the first optical microstructure 242a and the second optical microstructure 244a can also be two diffractive optical elements which are attached to or leaned against the first waveguide 232 and the second waveguide 234, respectively. Furthermore, in other embodiments, the first optical microstructure 242a and the second optical microstructure 244a can also be holographic optical elements (HOEs), computer-generated holographic optical element structures, fresnel lens structures or a lens gratings. In the present embodiment, a pitch between the first optical microstructure 242a and the second optical microstructure 244a (e.g., a pitch between two adjacent arc shape strips in the first optical microstructure 242a and the second optical microstructure 244a depicted in FIG. 3A, namely, a pitch between two adjacent strips in the diffractive optical element) falls, for example, within a range from 0.05 to 100 μm.

In the present embodiment, with proper design of the diffractive structure of the first optical microstructure 242a, energies of the first beam B1 and the second beam B2 from the first waveguide 232 can be concentrated into a diffractive light in one specific diffractive order (e.g., −1 order or +1 order). Therefore, the first beam B1 and the second beam B2 can be concentratedly irradiated towards different directions and on different positions of the biological tissue 50. Next, the second optical microstructure 244a can concentrate the energies of the first beam B1 and the second beam B2 from the biological tissue 50 into a diffractive light in one specific diffractive order (e.g., −1 order or +1 order). Therefore, the first beam B1 and the second beam B2 from the biological tissue 50 can be concentrated on the first light detector 222a and the second light detector 224a, respectively. Accordingly, the signal-noise ratio detected by the detecting device 100a can be effectively improved thereby improving accuracy and reliability of the detecting device 100a.

In the present embodiment, the calculating unit 110 can receive an electrical signal E1 from the first light detector 222a and an electrical signal E2 from the second light detector 224a. Therein, the electrical signal E1 corresponds to the light intensity of the first beam B1, and the electrical signal E2 corresponds to the light intensity of the second beam B2.

In the present embodiment, the first optical microstructure 242a and the second optical microstructure 244a are two separate structures. However, in other embodiments, the first optical microstructure 242a and the second optical microstructure 244a can also be manufactured on the same optical film.

Figure 4A:
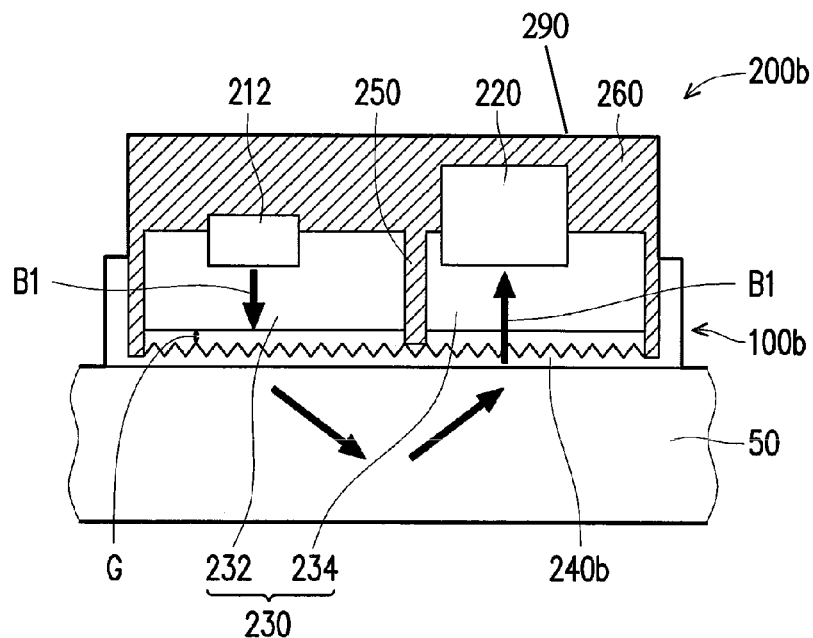
FIG. 4A and FIG. 4B are bottom schematic views of a detecting device according to yet another embodiment of the disclosure.
Figure 4B:
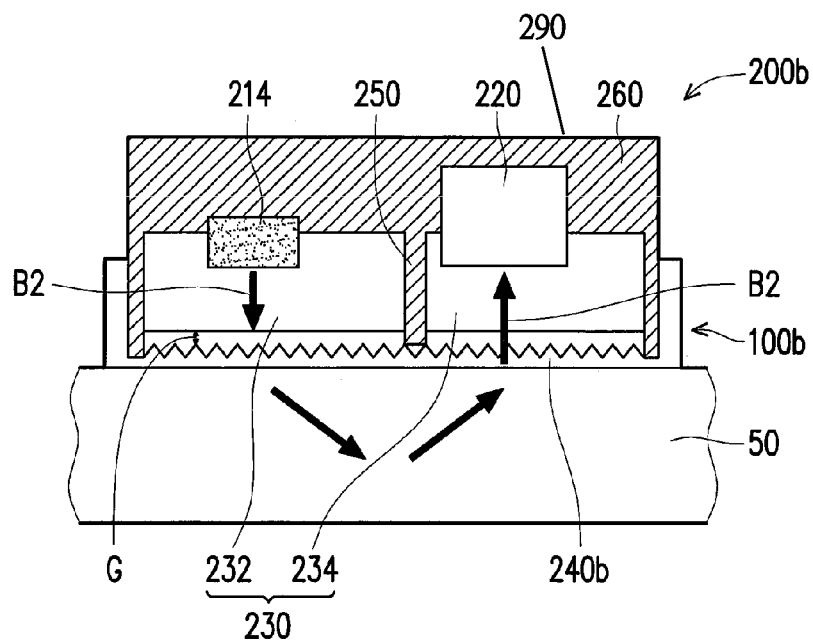

FIG. 4A and FIG. 4B are bottom schematic views of a detecting device according to yet another embodiment of the disclosure. Referring to FIG. 4A and FIG. 4B, a detecting device 100b of the present embodiment is similar to the detecting device 100 depicted in FIG. 1B and FIG. 1C, and the difference between the two is described as below. In a detecting module 200b of thedetecting device 100b, an optical microstructure unit 240b is spaced from the packaging unit 230 at a distance G. For instance, the optical microstructure unit 240b can be formed into a cap body which is fixed on the outer cover 260 and covering the first waveguide 232 and the second waveguide 234. The optical microstructure unit 240b can comprise a diffractive optical element structure, a holographic optical element, a computer-generated holographic element structure, a fresnel lens structure or a lens grating.

Figure 5A:
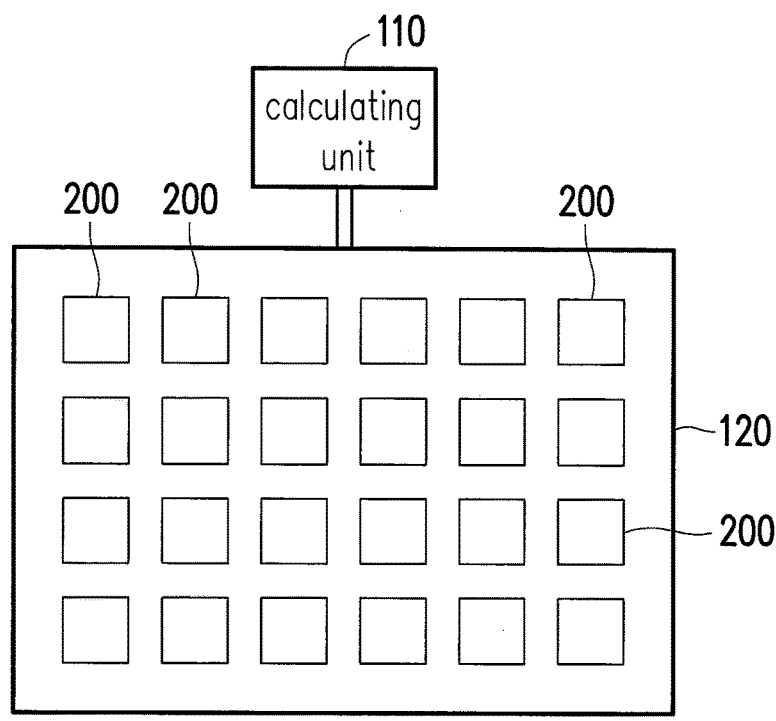
FIG. 5A to FIG. 5C are bottom schematic views of detecting devices according to three other embodiments of the disclosure.
Figure 5B:
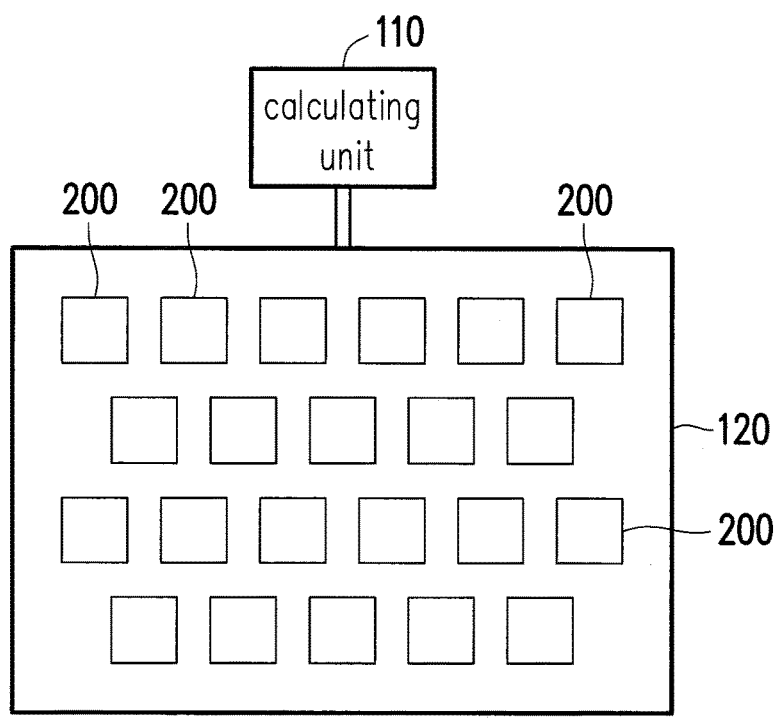
Figure 5C:
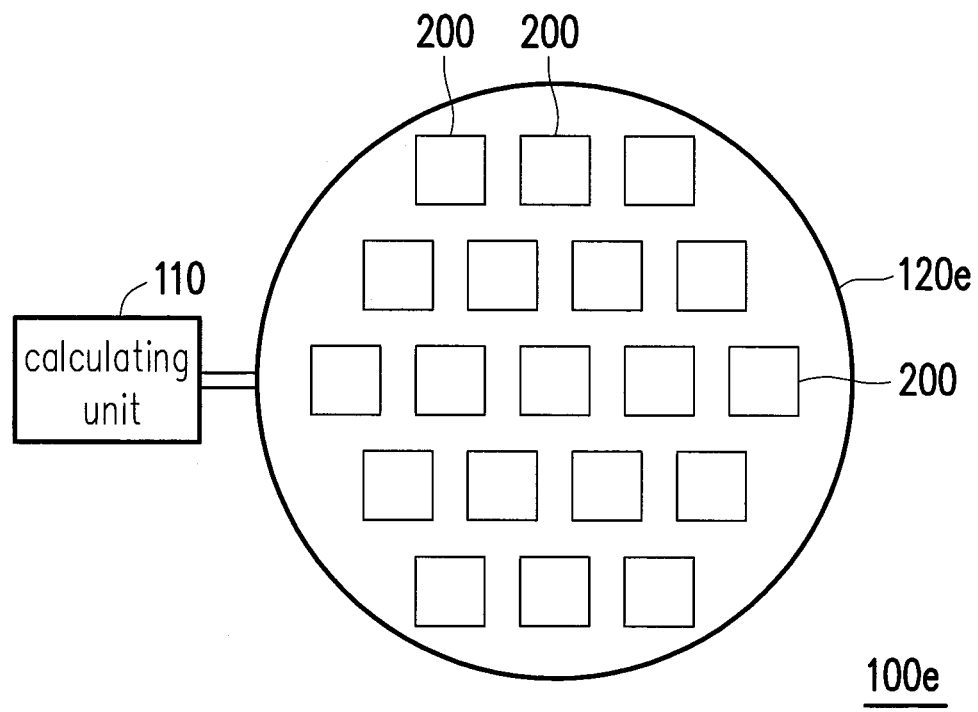

FIG. 5A to FIG. 5C are bottom schematic views of detecting devices according to three other embodiments of the disclosure. Referring to FIG. 5A to FIG. 5C, detecting devices 100c, 100d and 100e are similar to the detecting device 100 depicted in FIG. 1A, the differences therebetween is described as below. Each of the detecting devices 100c, 100d and 100e comprises a plurality of detecting modules 200, and the detecting modules 200 are arranged a two-dimensional array. Therein, detailed structure of each of the detecting modules 200 is identical to the detecting module 200 depicted in FIG. 1A, thus related description are not repeated hereinafter. The detailed structure of each of the detecting modules 200 is not illustrated again in FIG. 5A to FIG. 5C, and said detailed structure can refer to FIG. 1A and related description thereof.

In FIG. 5A, the detecting modules 200 are arranged in the two-dimensional array, and the detecting modules are fixed on a connecting piece 120. In FIG. 5B, the detecting modules 200 are arranged in a two-dimensional array of dislocation (e.g., a cellular two-dimensional array), and the detecting modules are fixed on a connecting piece 120. In FIG. 5C, the detecting modules 200 are arranged in the circular array, and the detecting modules are fixed on a connecting piece 120e. The connecting pieces 120 and 120e can be a flexible connecting piece, so that the detecting modules 200 can be bended along a shape of skin and to be attached on different positions of skin. Accordingly, physiological parameters (e.g., the blood oxygenation) at different positions of human body can be simultaneously monitored. If a number of the detecting module 200 is dense enough to form a physiological parameter image (e.g., a blood oxygenation image), a distribution status of the physiological parameter can be obtained. Shapes of the connecting pieces 120 and 120e may vary according to different shapes of the two-dimensional array. For instance, the connecting piece 120 is a rectangular shape, and the connecting piece 120e is a circular shape. However, in other embodiments, the detecting modules 200 can also be arranged in the two-dimensional array of other shapes, and the connecting pieces can also be of other shapes. In addition, the calculating unit 110 is electrically connected to the detecting modules 200 so as to perform calculations according to the light intensities detected by the detecting modules 200.

Moreover, the detecting modules 200 in the detecting devices 100c, 100d, 100e can be replaced by the detecting modules 200a or 200b in the previous embodiments, or the detecting modules in other embodiments.

In summary, in the detecting device of the embodiment of the disclosure, the optical microstructure unit is adopted to have the first beam and the second beam concentratedly irradiated on the biological tissue, and the optical microstructure unit is utilized to have the first beam and the second beam from the biological tissue concentratedly irradiated on the light detecting unit. Therefore, the signal-noise ratios of the first beam and the second beam measured by the light detecting unit are higher. Accordingly, the detecting device can have a lower error rate, a higher accuracy and a higher reliability. Moreover, as the signal-noise ratio being higher, it is not required for the calculating unit to adopt complex algorithms to reduce the noise, such that manufacturing cost and calculation time of the calculating unit can also be lowered.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A detecting device configured to detect a physiological parameter of a biological tissue, the detecting device comprising at least one detecting module, the detecting module comprising:
    a light source configured to emit a first beam and a second beam, wherein a wavelength of the first beam is different from a wavelength of the second beam;
    at least one light detector;
    a package disposed on the light source and the at least one light detector and located in transmission paths of the first beam and the second beam from the light source;
    an outer cover covering the light source, the at least one light detector and the package, and the outer cover comprising a top surface; and
    an optical microstructure located in the transmission paths of the first beam and the second beam, and arranged in parallel with the top surface of the outer cover;
    wherein the optical microstructure comprises a diffractive optical element structure;
    wherein the first beam and the second beam are emitted from the light source and are configured to pass through the package; upon passing through the package, the first beam and the second beam are configured to be diffracted from the diffractive optical element structure and transmitted to a biological tissue; upon transmission to the biological tissue, the first beam and the second beam are reflected from the biological tissue towards the diffractive optical element structure, the reflected first beam and the reflected second beam are configured to be diffracted from the diffractive optical element structure and pass through the package; upon passing through the package, the reflected first beam and the reflected second beam are configured to be transmitted to and be detected by the at least one light detector.

2. The detecting device of claim 1, wherein the package comprises a waveguide disposed on the light source and the at least one light detector.

3. The detecting device of claim 1, wherein the optical microstructure is mounted on the package.

4. The detecting device of claim 1, wherein the optical microstructure is spaced from the package.

5. The detecting device of claim 1, wherein the optical microstructure is formed on a surface of the package.

6. The detecting device of claim 1, wherein the optical microstructure comprises a holographic optical element, a computer-generated holographic element structure, a fresnel lens structure or a lens grating.

7. The detecting device of claim 1, wherein the package comprises:
    a first waveguide disposed on the light source; and
    a second waveguide disposed on the at least one light detector, wherein the detecting module further comprises a light separating body separating the first waveguide and the second waveguide.

8. The detecting device of claim 7, wherein the optical microstructure comprises a first optical microstructure aligned with the light source and a second optical microstructure aligned with the at least one light detector.

9. The detecting device of claim 1, wherein the light source comprises:
    a first light-emitting element configured to emit the first beam; and
    a second light-emitting element configured to emit the second beam, wherein the first light-emitting element and the second light-emitting element are configured to alternately emit the first beam and the second beam.

10. The detecting device of claim 1, wherein the at least one light detector comprises:
    a first light detector configured to detect the reflected first beam after the first beam being reflected from the biological tissue and transmitted through the optical microstructure and the package; and
    a second light detector configured to detect the reflected second beam after the second beam being reflected from the biological tissue and transmitted through the optical microstructure and the package; and
    the light source simultaneously emits the first beam and the second beam.

11. The detecting device of claim 10, wherein the light source comprises:
    a light-emitting element having a light-emitting surface and being configured to emit an original beam through the light-emitting surface, wherein a wavelength of the original beam is identical to the wavelength of the first beam; and
    a wavelength converting material covering a first portion of the light-emitting surface, and exposing a second portion of the light-emitting surface, wherein at least a part of the original beam emitted by the first portion is converted into the second beam by the wavelength converting material, and the first beam is formed by the original beam emitted by the second portion.

12. The detecting device of claim 1, wherein the optical microstructure comprises:
    a first optical microstructure disposed in the transmission paths of the first beam and the second beam from the light source, configured to transmit the first beam and the second beam from the light source to the biological tissue; and
    a second optical microstructure disposed in transmission paths of the first beam and the second beam reflected from the biological tissue, configured to transmit the reflected first beam and the reflected second beam from the biological tissue to the at least one light detector.

13. The detecting device of claim 1, further comprising a processor electrically connected to the at least one light detector, wherein the at least one light detector converts the first beam and the second beam being detected into an electrical signal, and the processor calculates the physiological parameter according to the electrical signal.

14. The detecting device of claim 1, wherein the physiological parameter is a blood oxygenation.

15. The detecting device of claim 1, wherein the at least one detecting module is a plurality of detecting modules, and the plurality of detecting modules are arranged in a two-dimensional array.

16. The detecting device of claim 1, wherein the wavelengths of the first beam and the second beam fall within wavelength ranges of a red light and an infrared light.

17. The detecting device of claim 1, wherein the light source and the at least one light detector are configured to be located at an identical side of the biological tissue.

* * * * *